(12) United States Patent
Hodges et al.

(10) Patent No.: US 6,193,865 B1
(45) Date of Patent: Feb. 27, 2001

(54) ANALYTIC CELL

(75) Inventors: Alastair McIndoe Hodges, Blackburn South; Oddvar Johansen, Mulgrave; Ronald Christopher Chatelier, Bayswater; Ian Andrew Maxwell, Five Dock; Thomas William Beck, North Richmond, all of (AU)

(73) Assignee: USF Filtration and Separations Group, Inc., Timonium, MD (US)

( * ) Notice: Subject to any disclaimer, the term of this patent is extended or adjusted under 35 U.S.C. 154(b) by 0 days.

(21) Appl. No.: 09/268,250

(22) Filed: Mar. 15, 1999

Related U.S. Application Data

(63) Continuation of application No. PCT/AU97/00599, filed on Sep. 11, 1997.

(51) Int. Cl.⁷ .................................................. G01N 27/401
(52) U.S. Cl. ........................ 204/435; 204/433; 205/787.5
(58) Field of Search .................................. 204/415, 416, 204/435, 433

(56) References Cited

U.S. PATENT DOCUMENTS

| | | | |
|---|---|---|---|
| 4,053,381 | * 10/1977 | Hamblen et al. ..................... | 204/416 |
| 4,100,048 | * 7/1978 | Pompei et al. ........................ | 204/415 |
| 4,224,125 | 9/1980 | Nakamura et al. . | |
| 4,233,029 | 11/1980 | Columbus . | |
| 4,254,083 | 3/1981 | Columbus . | |
| 4,259,165 | 3/1981 | Miyake . | |
| 4,301,412 | 11/1981 | Hill et al. . | |
| 4,301,414 | 11/1981 | Hill et al. . | |
| 4,303,887 | 12/1981 | Hill et al. . | |
| 4,307,188 | 12/1981 | White . | |
| 4,374,013 | 2/1983 | Enfors . | |
| 4,404,066 | 9/1983 | Johnson . | |
| 4,431,004 | 2/1984 | Bessman et al. . | |
| 4,517,287 | 5/1985 | Scheibe et al. . | |
| 4,517,291 | 5/1985 | Seago . | |
| 4,629,563 | 12/1986 | Wrasidlo . | |

(List continued on next page.)

FOREIGN PATENT DOCUMENTS

| | | |
|---|---|---|
| 31042/93 | 7/1993 | (AU) . |
| 54873/94 | 8/1994 | (AU) . |
| 3103464 | 8/1982 | (DE) . |
| 43 12 126 A1 | 10/1994 | (DE) . |
| 0 215 446 A2 | 3/1987 | (EP) . |
| 0 231 033 A2 | 8/1987 | (EP) . |
| 0 251 915 A2 | 1/1988 | (EP) . |
| 0 255 291 A1 | 2/1988 | (EP) . |
| 0 266 204 A2 | 5/1988 | (EP) . |
| 0 278 647 A2 | 8/1988 | (EP) . |
| 0299779 | * 1/1989 | (EP) . |
| 0 351 516 A2 | 1/1990 | (EP) . |
| 0 351 892 A2 | 1/1990 | (EP) . |
| 0 170 375 | 5/1990 | (EP) . |
| 0 451 981 A2 | 10/1991 | (EP) . |
| 59-3345 | 1/1984 | (JP) . |
| 6-222874 | 10/1987 | (JP) . |
| 3-167464 | 7/1991 | (JP) . |
| 4-62463 | 2/1992 | (JP) . |
| 6-34600 | 6/1994 | (JP) . |
| WO 89/08713 | 9/1989 | (WO) . |
| WO 95/16198 | 6/1995 | (WO) . |
| WO 95/28634 | 10/1995 | (WO) . |
| WO 97/00441 | 1/1997 | (WO) . |

*Primary Examiner*—T. Tung
(74) *Attorney, Agent, or Firm*—Knobbe, Martens, Olson, and Bear, LLP

(57) ABSTRACT

Electrochemical cell having a porous substrate and a first and a second electrodes separated by an ion diffusion inhibiting partition is disclosed. The ion diffusion inhibiting partition between the two electrodes is defined by compressing the substrate and/or blocking pores of the substrate so as to inhibit but not entirely block ion diffusion between the two electrodes.

10 Claims, 3 Drawing Sheets

U.S. PATENT DOCUMENTS

| | | |
|---|---|---|
| 4,774,039 | 9/1988 | Wrasidlo . |
| 4,988,429 | 1/1991 | Matthiessen . |
| 5,064,516 | 11/1991 | Rupich . |
| 5,314,605 * | 5/1994 | Matthiessen ........................ 204/415 |
| 5,413,690 | 5/1995 | Kost et al. . |
| 5,540,827 | 7/1996 | Deacon et al. . |
| 5,980,709 * | 11/1999 | Hodges et al. ....................... 204/409 |

* cited by examiner

ANALYTIC CELL

This application is a continuation of International Application No. PCT/AU97/00599, filed on Sep. 11, 1997.

This invention relates to the determination of ionic activities and/or concentrations in a solution containing ions.

BACKGROUND OF THE INVENTION

The determination of activities or concentrations of ions in general and of the hydrogen ion (pH) in particular is routinely required in the chemical industry, in laboratories, and increasingly in homes (eg for the assessment of soil, pH, and swimming pool chlorination).

It has been practised to use litmus or universal indicator paper to estimate solution pH. Litmus paper is paper coated with one or more indicator dyes that change colour according to the pH of a sample in contact with the strip. The strips are then compared with a colour chart to estimate the pH. Litmus strips are relatively inexpensive and are discarded after use. The strips are easy to use, do not require calibration, and are readily portable, but have low resolution, are not useful with coloured liquids, are subject to user error, and cannot be used by colour-blind persons.

The primary method employed for accurate measurement of pH is the pH meter. The pH meter is based in principle on the measurement of electrode potential in a reversible galvanic or voltaic cell. A galvanic or voltaic cell consists of two electrodes in contact with a solution and combined in such a manner that when the electrodes are connected by an electric conductor an electric current will flow. At the interface of the electrode and the solution there exists an electrical potential call the "electrode potential". The electromotive force of the cell is then equivalent to the algebraic sum of the two electrode potentials (appropriate allowance being made for the sign of each potential difference). For reliable measurement of the EMF of such a cell it is necessary to use some form of potentiometer, for example a wheatstone bridge circuit calibrated against a reference cell of known EMF. Such cells may be chemical cells in which an overall chemical reaction takes place or "concentration" cells in which there is a change of energy due to the transfer of solute from one concentration to another. For the electrical energy produced in the cell to be related thermodynamically to the process occurring in the cell, the cell should behave reversibly in a thermodynamic sense.

Such an electrochemical cell consists of two single electrodes or half cells. For example a standard metal—metal ion electrode and a standard hydrogen electrode form a cell which is written as follows:

$$M;M^+(a=1) \;f\; H^+(a=1);H_2(1\ atm),Pt \quad (1)$$

where the vertical parallel bars indicate that the junction potential between the two different electrolytic solutions is practically eliminated by connection through a diffusion barrier, for example, a salt bridge, a frit, capillary, or the like means which allows electrical connection in solution but prevents convection and restricts diffusion of ionic species. When the concentration of the ions is such that their activity is unity, as indicated in the cell of Equation 1 by a=1, the electrode potential is designated as $E^0$ and is equal to the standard oxidation potential. The voltage of a cell is the algebraic sum of the oxidation potential for the electrode written at the left and the reduction potential of the electrode written at the right. By convention the chemical reaction corresponding to a given cell is written so that the electrons move from left to right outside the cell.

The electrode potential changes with the activity of the ions. The fundamental equation governing the effect of activity of ions on the voltage is:

$$E = E^\circ - \frac{RT}{nF}\ln Q \quad (2)$$

where T is the temperature
R=gas constant, 8.314 Joules deg$^{-1}$, mole$^{-1}$
F=Faraday, 96,486.7 Coulombs, equiv$^{-1}$
n=number of electrons for the reaction as written
Q=activity quotient $$Q = \frac{a_G^g \; a_H^h}{a_A^a \; a_B^b}$$

for the generalised reaction $$a\,A + b\,B = g\,G + h\,H \quad (3)$$

It may be shown that in a single junction liquid cell with a hydrogen electrode and a reference electrode, for example a calomel electrode, the pH is defined by $$pH = pH(S) + \frac{E - Es}{2.3026RT/F} \quad (4)$$

where E is the measured EMF for an unknown solution in the cell, R, T and F are as previously defined, pH(S) is the assigned pH value of a standard reference solution and $E_s$ is the EMF measured when this reference solution replaces an unknown solution in the cell described.

Three types of electrode have been used in cells of the kind under discussion for the measurement of hydrogen and other ionic concentration. The first type of reversible electrode includes a metal or a non-metal in contact with a solution of its own ions, eg zinc in zinc sulphate solution, or copper in copper sulphate solution. Non metals which, at least in principle, yield reversible electrodes are hydrogen, oxygen and the halogens, the corresponding ions being hydrogen, hydroxyl and halide ions respectively. Since the electrode materials in these cases are non-conductors, and often gaseous, finely divided platinum or other noble metal which comes rapidly into equilibrium with the hydrogen, oxygen etc has been employed for the purposes of making electrical contact. The classic hydrogen electrode which is the primary standard for all measurements of hydrogen ion concentration is an example of this first class of electrode. It consists of a small sheet of platinum coated with platinum black. In use this electrode is immersed in a solution and pure hydrogen is bubbled over the surface for at least 20–30 minutes. Although of importance as a standard, the hydrogen electrode is not practical for everyday use and is readily poisoned by species such as arsenic, heavy metals, sulphides and cyanides.

Electrodes of the second type involve a sheet or wire of metal and a sparingly soluble salt of this metal in contact with a solution of a soluble salt of the same anion. An example is an electrode consisting of silver, solid silver chloride and a solution of a soluble chloride, such as potassium chloride. These electrodes behave as if they were reversible with respect to the common anion namely the chloride ion in this case. Electrodes of this type have been made with other insoluble halides eg silver bromide and iodide and also with soluble sulphates, oxalates etc. Calomel electrodes are of this kind.

A third type of reversible electrode consists of a sheet of an inert metal, for example, gold or platinum, immersed in a solution containing both oxidised and reduced states of an oxidation reduction a system ("redox" system) for example $Sn^{++++}$ and $Sn^{++}$, $Fe^{+++}$ and $Fe^{++}$ or $Fe(CN)_6^{3-}$ and $Fe(Cn)_6^{4-}$. The oxidised and reduced states are not necessarily ionic. For example oxidation-reduction electrodes involving organic compounds are known for example the Quinhydrone electrode. Quinhydrone is an equimolecular compound of hydroquinone, $HOC_6H_4OH$, and benzoquinone, $OC_6H_4O$. At 25° C. this is dissociated to an extent of about 93% into its two components. An electrode is formed by immersing a bright inert metal such as platinum or gold in a solution (usually saturated) of Quinhydrone.

The solution needs to be freshly prepared and moreover freshly recrystallised Quinhydrone should be used in its preparation. The Quinhydrone electrode was used extensively in the 1920s but due to the inconvenience of its preparation and short solution shelf life it was rapidly superseded when the calomel electrode was developed.

The development of the glass pH electrode resulted in an electrode which far surpassed all those previously used and made practical the pH meter as now widely used. The glass electrode could be used successfully in oxidising or reducing mediums, in the presence of heavy metals, and in mixtures in which the hydrogen, quinone, and antimony electrodes would not give repetitively accurate results. In its simplest form the glass electrode consists of a thin-walled glass bulb with an inner solution in which a reference electrode is immersed. For general use the electrode is usually blown from a special glass (such as Corning 015 glass) which has a low melting point, high hygroscopicity, and relatively high electrical conductivity. The potential of a glass electrode depends upon the nature of the inner electrode and the composition of the inner solution as well as the "asymmetry potential". Because the glass electrode was suitable for mass manufacture, was relatively robust, and of long life, it became widely used for the measurement of pH. Meters utilising the glass electrode are accurate and cheap to operate. However because the glass electrode is of intrinsically high resistance an electronic voltmeter is required, and the meters are not always portable. Furthermore such pH meters require tedious calibration which involves the cost of consumable buffer solutions as well as the expenditure of valuable operator time.

PCT/GB87/00857 describes a hollow capillary fill cell having electrodes on interior surfaces of the cell and having reagents "printed" onto interior surfaces of the cell. The distance between the electrodes is significant because the cell relies on the spatial separation between the electrodes to act as a capillary or frit. That is to say the distance between the electrodes must be such that diffusion of ions from one electrode to the other takes longer than the test.

OBJECT OF THE INVENTION

An object of the present invention is to provide inexpensive means to facilitate the convenient measurement of pH which avoid or at least ameliorate disadvantages of the prior art. Preferred embodiments of the invention are useful for estimating the activity and/or concentration of ionic species in solution and/or redox potentials

DESCRIPTION OF THE INVENTION

According to one aspect the invention consists in a cell comprising a first electrode, a reference electrode, a porous membrane extending between the first electrode and the reference electrode for retaining a liquid analyte if admitted to the porous membrane in electrical contact with both said electrodes.

a redox chemical system (as herein defined) contained in the porous membrane, and a diffusion barrier disposed between said electrodes.

Desirably the diffusion barrier is formed in the porous membrane by compressing a volume thereof and/or by loading a blocker into the pores of a volume thereof. The degree of compression and/or the extent of the pore blocking are selected so as to result in a barrier to diffusion which nevertheless provides electrical connection between solutions on both sides of the barrier and functions in a manner similar to a frit.

In our copending application Ser. No. 08/973,086, now issued on Nov. 9, 1999, as U.S. Pat. No. 5,980,709 (the disclosure of which is incorporated herein by reference) there is described a method for defining an area of a coating or layer attached to a porous substrate. By compressing the substrate and/or by blocking pores of the substrate in a region of the substrate there is formed a barrier which substantially prevents migration of a liquid through the barrier that is to say from the substrate on one side of the region to the substrate on the other side of the region. As described in said application the method is used to precisely define the boundary of an electrode area. It has now been found that a barrier may be formed in a similar manner and which resists ionic diffusion but permits electron migration and so is able to function in a manner similar to a frit.

In preferred embodiments the present invention provides a single use disposable apparatus comprising a "cell" with integral electrodes and containing dried redox chemicals, the apparatus being packaged in a waterproof container for example a foil sachet. In use, the apparatus is removed from the waterproof container and is electrically connected eg by a plug and socket connection, to a potentiometer or EMF measuring device. A solution to be tested is then applied to a "target area" on the apparatus and is drawn into the cell. The analyte dissolves the dried redox chemicals and comes into contact with both electrodes. The potential between the electrodes is then measured by the potentiometer and may be displayed by analogue or digital means continuously or after a predetermined interval. The apparatus comprising the cell and the electrodes is then spent and may be disposed of or recycled for recovery of component parts.

In more highly preferred embodiments the apparatus further comprises a reference cell which may contain buffer chemicals as well as redox chemicals. The buffer chemicals may be in dried form and separated from eg a distilled water reservoir by a frangible barrier. The barrier may be broken to dissolve the chemicals in the reference cell enabling the electrodes adjacent the reference cell to be calibrated. Alternatively, water may simply be introduced into the reference cell from an external supply when required. By assuming that the electrodes adjacent the analyte cell are identical with those adjacent the reference cell and measuring the EMF of both cells a more accurate measure of an ion concentration in the analyte may be obtained.

Cells according to the invention may be used to measure pH, concentration of other ions (eg chloride), to estimate ion activity, to measure conductivity, to estimate free energy, and to perform potentiometric titrations and the like.

BRIEF DESCRIPTION OF THE DRAWINGS

Various embodiments of the invention will now be described by way of example only with reference to the accompanying schematic (not to scale) drawings wherein.

DESCRIPTION OF PREFERRED EMBODIMENTS

Figure 1:
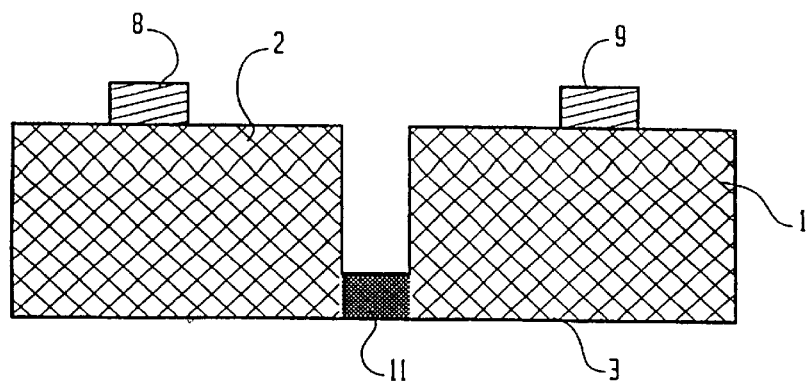
FIG. 1 shows a first embodiment of the invention in end elevation cross-section on line 1—1 of FIG. 2.

With reference to FIG. 1, there is shown a first embodiment of the invention which comprises a porous membrane 1 defining a substantially rectangular cell volume between a top membrane surface 2, a bottom membrane surface 3, membrane side surfaces 4, 5 and end surfaces 6, 7. Membrane 1 may for example be formed from a sheet of polysulphone or polyvinylidinedifluoride. The sheet may for example have a thickness of 100 microns and pore size of, for example, 0.2 microns.

The cell has a first electrode 8 which is in the form of a thin film of metal, for example, of gold or platinum, deposited for example by sputtering on the exterior of one side 2 of membrane 1. A second (reference) electrode 9 is formed, for example, adjacent first electrode 8 and spaced apart from it on the same side 2 of membrane 1 as first electrode 8. Alternatively, electrode 9 may be on the opposite side 3 of porous membrane 1 defining a cell therebetween with electrode 8.

Between electrodes 8, 9 a diffusion barrier 11 is formed by compressing porous membrane 1 from one or both of sides 2, 3 to form a barrier at a location intermediate electrodes 8, 9. In the example of FIG. 1 the barrier is formed by compression from one side and extends from one end 6 to the other end 7 (FIG. 2) intermediate electrodes 8, 9. Barrier 11 may be formed before or after the electrodes are assembled with, or deposited upon, membrane 1 but preferably is formed prior to applying the electrodes. To form barrier 11 pressure is applied selectively to compress the membrane so that the density of the membrane material in the barrier region is increased to an extent that ion diffusion across the resulting compressed region is significantly reduced in comparison with diffusion through the uncompressed membrane but sufficient to allow electrical connection across the compressed region. In the present example that is achieved by applying pressures in the range of 50–125 KPa. Alternatively, barrier 11 may be formed by chemically blocking pores of the membrane in a confined region or by a combination of chemical and physical means as described in U.S. Pat. No. 5,980,709.

Second electrode 9 is a reference electrode and may, for example, be a silver electrode which is sputter deposited and is subsequently treated to form a silver halide or, for example, is treated with chlorine or electrochemically in a solution containing chloride ions, or by use of hypochlorite, or an with oxidant in the presence of chloride, or other treatment to form a silver chloride, or is oxidised or allowed to oxidise to form a silver oxide surface. The metal is then reacted with a halogen to form in situ a metal/metal halide reference electrode, for example, a silver/silver chloride electrode. Surprisingly, it has been found that electrodes formed in this manner are able to reach a steady state potential within 30 seconds, and typically within 10 seconds, when placed in, for example, a solution containing the chloride. Because the reference electrode has a relatively non-porous surface it equilibrates rapidly with the solution and reaches a steady state potential within 30 seconds, more usually within 10 seconds. This facilitates measurement using small sample volumes (for example a few microliters) and provides high reproducibility and accuracy. It also enables cells to be made inexpensively with much smaller variation both within batches and between batches than hitherto possible. Moreover, because measurements can be obtained rapidly, measurements of pH can be made using the hydroquinone redox system at a pH of above 8.

Desirably electrodes 8, 9 are connected to or are integral with connectors 10 whereby the assembly may be conveniently electrically connected with interengaging connectors of apparatus (not illustrated) for measuring the potential or potential difference (eg a voltmeter of suitable impedance).

A redox system, for example, quinone-hydroquinone is deposited on or in the membrane, for example between barrier 11 and electrode 8. The chemicals may, for example, be deposited by means of a micro pipette as a solution which is subsequently evaporated leaving the chemicals as a dry deposit.

In preferred embodiments of the invention there is provided a cell having two chemical systems, for example a reference electrode 8 comprising silver/silver chloride has potassium chloride dried in the membrane on the side of barrier 11 adjacent reference electrode 9 while the side of barrier 11 adjacent first electrode 8 has hydroquinone deposited in the membrane. Because the redox electrode is separated from the reference electrode by means 11 which act as a barrier to solution mixing while allowing an ionic connection between the electrodes the need for a substantial spacing between the electrodes is avoided and a more compact assembly is made possible. It will be understood that the diffusion barrier should prevent substantial mixing but not totally prevent ionic diffusion. It is sufficient that the barrier slows diffusion to an extent such that substantial quantities of ions do not diffuse from one electrode to the other during the time of a test.

Figure 2:
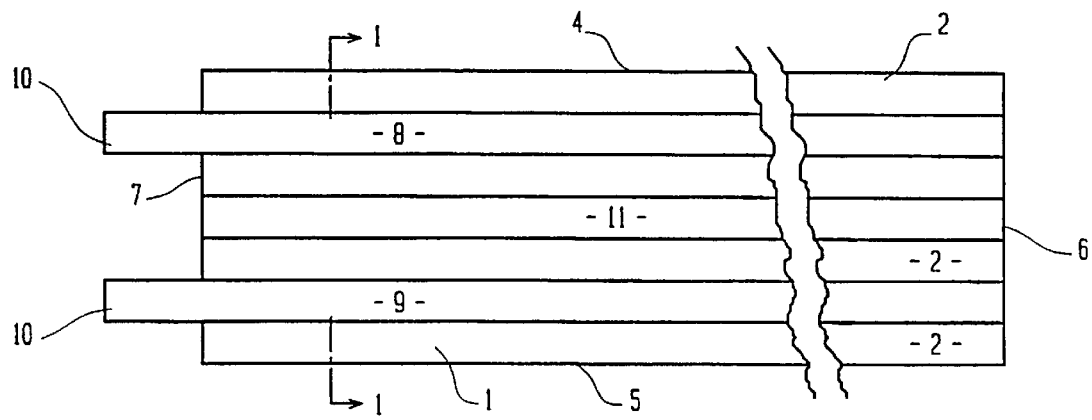
FIG. 2 shows the first embodiment in plan, viewed from above.
Figure 3:
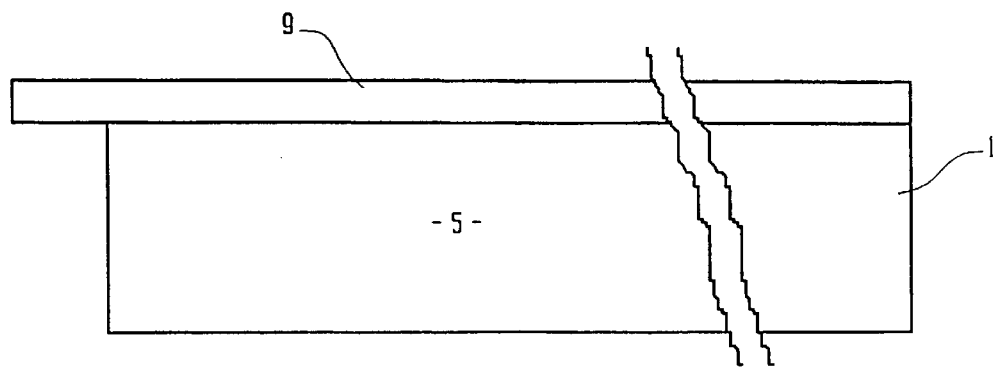
FIG. 3 shows the embodiment of FIG. 1 in side elevation.
Figure 4:
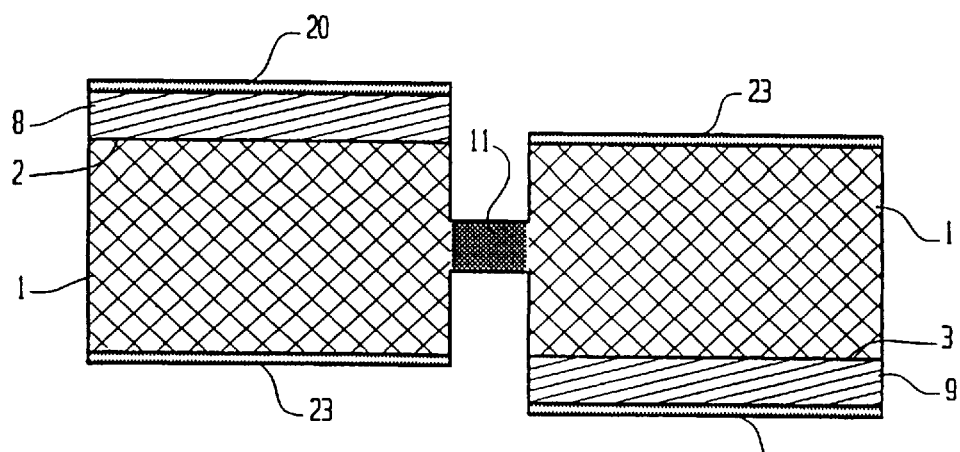
FIG. 4 shows a second embodiment of the invention in end elevation cross-section.

With reference to FIG. 4 there is shown a second embodiment similar to that of FIGS. 1 to 4 wherein the same numerals are used to identify parts of function corresponding to parts of FIGS. 1–3. The embodiment of FIG. 4 differs from that of FIG. 1 in that electrodes 8, 9 are disposed on opposite sides of membrane 1 and are differently assembled with the membrane. The embodiment of FIG. 4 comprises a porous membrane 1 assembled with a Mylar carrier film 20 on which is sputter deposited a thin film of platinum metal 8, film 20 being mounted on one face of membrane 1 with metal 8 in contact with surface 2 of membrane 1. A second Mylar carrier film 21 on which is sputter deposited a coating of silver a surface 9 of which has been converted to silver chloride, is mounted with its silver chloride surface 9 in contact with second surface 3 of membrane 1. Diffusion barrier 11 is formed between electrodes 8, 9, by compression from both sides of membrane 1 in the embodiment of FIG. 4 but may be formed for example, by selective chemical blocking or compression of a region of membrane 1 in the manner described in U.S. Pat. No. 5,980,709 or by a combination of chemical treatment and compression. Diffusion barrier 11 in effect divides membrane 1 into two half cells. The degree of compression and/or chemical treatment at 11 are again selectively adjusted to control diffusion rate so that barrier 11 acts as an ion "bridge" while acting as a barrier to mixing. In the embodiment described in FIG. 4, membrane 1 on the side of barrier 11 adjacent silver chloride reference electrode 9 contains dried potassium chloride while membrane 1 on the side of barrier 11 adjacent platinum electrode 8 contains quinone/hydroquinone. A protective film or coating 23 may be provided on faces of the membrane which are not covered by electrodes.

If preferred, electrodes 8, 9 may be arranged in other dispositions and additional reference, or other electrodes may be employed.

Chemicals may be introduced to the cell either by injection with subsequent drying, or the chemicals may be printed onto one or more of the membrane surfaces prior to or after emplacing the electrodes.

It will be understood that the electrodes may comprise any suitable metal or metal/redox combination. As will be apparent to those skilled in the art the electrodes may be made of zinc, iron, cadmium, cobalt, nickel, tin, platinum, palladium, silver, copper, carbon, or the like. Platinum, palladium and gold are preferred as the first electrode. The reference electrode may be a silver/silver halide, or may be a metal/metal oxide system for example antimony, iridium, palladium in contact with their oxides. The preferred redox system is hydroquinone/quinone but other known redox combinations may be employed. Although preferred embodiments of the invention use Mylar as a supporting substrate for sputter deposited electrodes other chemically inert and electrically resistive substrates such as glass, ceramics, or plastic compositions may be employed.

The silver sputtered reference electrode may be treated as previously described to form a silver chloride surface. Similar treatments may be applied using silver or other reference electrode metals and other halogenation or oxidising agents.

Figure 5:
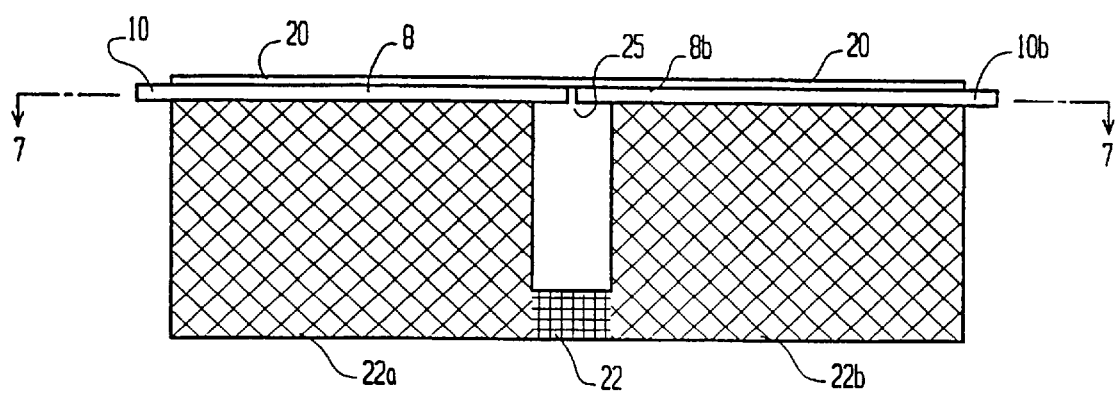
FIG. 5 shows a third embodiment of the invention in a side elevation cross-section on line 5—5 of FIG. 7.
Figure 6:
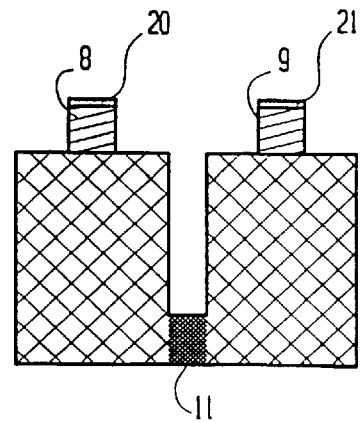
FIG. 6 shows the embodiment of FIG. 5 in end elevation.
Figure 7:
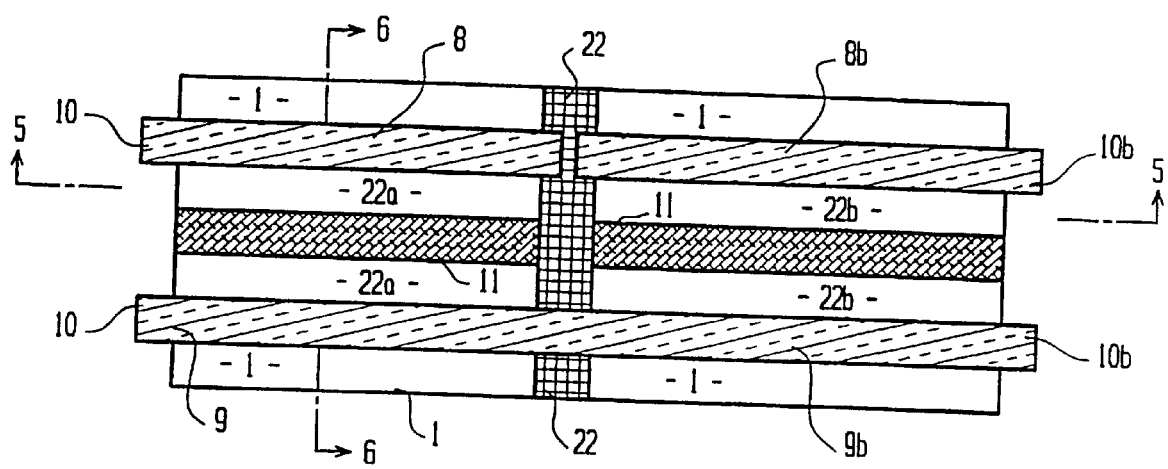
FIG. 7 shows a plan view of the embodiment of FIG. 5 on line 7—7 of FIG. 5.

A third embodiment will now be described with reference to FIGS. 5–7 in which there is shown a cell similar to those described above with reference to FIGS. 1–3. In FIGS. 5–7 parts having a function corresponding to those of parts in FIGS. 1–3 are identified by corresponding numerals. In the third embodiment the membrane is compressed and/or chemically blocked at a region 22 (FIG. 5) so as to divide membrane 1 into two cell volumes 22a and 22b. Region 22 is formed as described in U.S. Pat. No. 5,980,709 so as to effectively prevent liquid diffusion between cells 22a, 22b and thus performs a different function from partition 11 which substantially separates each cell into half cells between electrodes 8, 9. Region 22 extends the width of the cell, separating partition 11 into two sections which are electrically isolated by region 22. Each section of partition 11 functions as a ion diffusion inhibiting partition to its respective separated cell (FIG. 7). Cell 22b provides a second or independent "reference" cell. First electrodes 8 on carrier film 20 is divided at 25 into intermediate cell 22a and 22b. Cell 22b thus has an electrode 8b which is formed simultaneously with electrode 8 but which is subsequently electrically isolated from electrode 8 of the adjacent cell 22a. Reference electrode 9b may also be electrically isolated from electrode 9 but preferably a single continuous reference electrode common to both cells is employed (as in FIG. 7). In this embodiment calibration chemicals, for example, comprising a buffer, are deposited and dried in the second cell 22b. In use moisture is added to the second cell and the apparatus is plugged into an EMF measuring device via connectors 10b so that the potential between the first electrode 8b and reference electrode of reference cell 22b can be measured whereby the apparatus may be calibrated. The assembly is then connected to an EMF measuring device by means of connectors 10 so that the potential between electrodes 8, 9 of the analyte cell 22a may be measured. Analyte is added to first cell 22a and the potential of cell 22a containing the analyte is then measured. More preferably, the leads from both cells are arranged for connection to an EMF device capable of measuring or comparing the potential in both cells simultaneously. Because the dimensions of cells 22a and 22b may be easily reproduced with considerable precision, and because both cells are constructed virtually simultaneously, the apparatus may be manufactured with little variation in the electrodes as between the first and the second cell. Consequently, measurements in the analyte may be made with considerable accuracy.

In manufacture of devices according to the invention a continuous length of membrane material in the form of a strip may be divided into cells by compression and/or chemical blocking at intervals and each cell may be partitioned in the manner herein described. Electrodes may then be applied in continuous lengths, reagents deposited therein as desired and the continuous strip may subsequently be severed into individual cells or combinations of cells for packaging.

It will be understood that chemicals may be deposited by other means, for example, may be printed in or on the cell surfaces by means of a dot matrix print head. Practical embodiments of the invention are provided with plug or socket connectors to facilitate electrical connection of the sputtered electrodes with EMF measuring apparatus. Leads may be taken out at opposite ends or at one end of the assembly. If desired, a temperature measuring device eg a thermocouple or thermistor may be made an integral part of the apparatus. If desired, each device or sample from each batch may be calibrated before introduction of chemicals and in that case a calibration constant may be derived and marked on the device, for example, as a barcode which can be read automatically when the electrode assembly is connected to the voltage measuring device. This allows the measurement made to be automatically compensated for any variation in electrode construction.

When silver chloride electrodes made as herein described are connected in a cell with a standard silver chloride electrode the potential difference of less than 0.5 millivolts can be achieved. The variation between cells is much less. A steady state is evident within about 2 seconds. Measurements can be made using the Quinhydrone redox system a pH above 8. Such measurements are made by comparison with solutions of known pH are possible in view of the short time required to obtain a steady reading during which time the Quinhydrone does not undergo significant reaction.

As will be apparent to those skilled in the art from the teaching hereof features of one embodiment may be combined with those of another without departing from the scope of the invention herein disclosed. It will be understood that references to Quinhydrone herein are not limited to a 1:1 mixture of hydroquinone and quinone and that any composition comprising sufficient hydroquinone and quinone to establish a definite redox potential at the electrode may be used. Likewise, redox systems based on other quinones, for example, 1,4 naphthoquinone, tetrachlorobenzoquinone, thymoquinone, toluquinone and other alternative redox systems may be employed.

Apparatus according to preferred embodiments of the invention are portable and need not use mains power. Preferred embodiments need not employ calibration and no external calibration solutions are required. In preferred embodiments a single pH value is exhibited rather than a drifting value. Measurement may be made on small sample volumes, for example, less than a microliter.

As will be apparent to those skilled in the art from the teaching hereof apparatus according to the invention may be adapted for use with the measurement of specific ion concentrations other than hydrogen ion, other thermodynamic variables, for example free energy, conductivity, etc and may be manufactured in other forms and by other means.

What is claimed is:

1. A cell comprising a first electrode, a reference electrode, a porous membrane extending between the first electrode and the reference electrode for retaining a liquid analyte if admitted to the porous membrane in electrical contact with both said electrodes, and an ion diffusion inhibiting partition disposed between said electrodes, wherein said partition comprises a compressed and/or chemically blocked region of the membrane, and wherein said partition inhibits but does not entirely block ion diffusion.

2. A cell according to claim 1 wherein the electrodes are disposed on the same side of the membrane as each other.

3. A cell according to claim 1 wherein the reference electrode is silver/silver halide.

4. A cell according to claim 3 wherein the reference electrode is formed by sputter coating silver onto a supporting film and treating the silver to form a silver halide.

5. A cell according to claim 1 wherein the porous membrane on the side of the partition adjacent the reference electrode contains a soluble halide salt.

6. A cell according to claim 1 wherein the porous membrane on the side of the partition adjacent the first electrode contains a redox system.

7. A cell according to claim 6 wherein the redox system is a quinone-hydroquinone system.

8. A cell according to claim 1 wherein an electrode is formed on a carrier film prior to being assembled with the porous membrane.

9. A cell according to claim 1 wherein the cell is segregated by means of a region into two separate cells having two separate ion diffusion inhibiting partitions, wherein said region comprises a compressed and/or chemically blocked region of the membrane, and wherein said region electrically isolates the two separate cells thus formed.

10. A cell according to claim 1 in combination with apparatus for measuring the electrical potential difference between the electrodes.

* * * * *